United States Patent [19]

Connor et al.

[11] 4,225,722
[45] Sep. 30, 1980

[54] PROCESS FOR THE PRODUCTION OF 2-(1H-TETRAZOL-5-YL)-9-HYDROXY-1-OXO-1H-NAPHTHO-(2,1-B) PYRAN AND INTERMEDIATES THEREFOR

[75] Inventors: David T. Connor, Ann Arbor, Mich.; Patricia A. Young, Madison, N.J.; Maximilian Von Strandtmann, New Castle, Del.

[73] Assignee: Warner-Lambert Company, Morris Plains, N.J.

[21] Appl. No.: 841,782

[22] Filed: Oct. 13, 1977

[51] Int. Cl.$^2$ .......................................... C07D 405/04
[52] U.S. Cl. .................................. 548/253; 560/139; 260/345.2
[58] Field of Search .................... 260/308 D, 462 C, ; 560/141; 200/345.3, 606.5 B; 548/253

[56] References Cited

PUBLICATIONS

Patai, "Chemistry of the Cyano Group", p. 351, (1962), Interscience, N.Y.
Topchiev et al., "Boron Fluoride and Its Compounds as Catalysts in Organic Chemistry", p. 286, Permagon, N.Y., (1959).

Primary Examiner—Donald G. Daus
Assistant Examiner—D. B. Springer
Attorney, Agent, or Firm—Albert H. Graddis; George M. Kaplan

[57] ABSTRACT

This invention relates to Compounds of formula II:

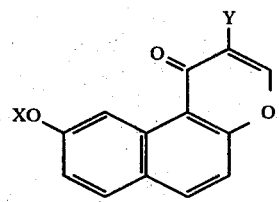

wherein Y is formyl, carboxylic acid, acrylic acid, cyano or tetrazolo; X is hydrogen, lower alkanoyl or lower alkyl, and their non-toxic, pharmaceutically acceptable salts are disclosed. These compounds are useful in the prevention of allergic and asthamatic reactions.

4 Claims, No Drawings

PROCESS FOR THE PRODUCTION OF 2-(1H-TETRAZOL-5-YL)-9-HYDROXY-1-OXO-1H-NAPHTHO-(2,1-B) PYRAN AND INTERMEDIATES THEREFOR

BACKGROUND OF THE INVENTION

1. Field of the Invention

The present invention relates to process for the production of 2-substituted-9-hydroxy-1-oxo-1H-naphtho[2,1-b]pyrans and 2-substituted-9-acetoxy-1-oxo-1H-naphtho[2,1-b]pyrans and the compounds produced thereby.

2. Disclosure of the Prior Art

Structurally distinct gamma-pyrone-3-carboxaldehyde derivatives are disclosed in the following United States patents: U.S. Pat. No. 3,887,585 and a division thereof, U.S. Pat. No. 3,959,480; U.S. Pat. No. 3,862,144 and a division thereof, U.S. Pat. No. 3,936,488; and U.S. Pat. No. 3,886,183. The fusion between the pyran ring and the naphthalene ring in certain of the compounds disclosed in aforementioned patents occurs at the [1,2-b] position or at the [2,3-b] position. If the compounds of the subject invention, this fusion is at the [2,1-b] position. Thus structurally distinct chemical compounds are provided.

Naphthodioxaborin intermediates are also disclosed in aforementioned United States patents which are structurally distinct from the naphthodioxaborin intermediate of the subject invention, since a corresponding difference in ring fusion is present.

Additionally, processes are described in aforementioned United States patents for obtaining the naphthodioxaborin intermediates and the gamma-pyrone-3-carboxaldehyde derivatives disclosed. However, no processes are disclosed in these patents for obtaining the structurally distinct compounds of the subject invention.

G. A. Reynolds and J. A. Van Allan, in *J. Het. Chem.* 6:375–377 (June, 1969) disclose an unsubstituted 3-formyl-benzo[f]chrom-4-one (designated compound 10) which has the same ring system as the final compounds of the subject invention. Also disclosed is an unsubstituted naphthodioxaborin intermediate (designated compound 4) from which compound 10 is prepared. In an earlier paper by these same authors (Van Allan, J. A. and Reynolds, G. A., *J. Het. Chem.* 6:29-35 (February, 1969)), the preparation of the unsubstituted naphthodioxaborin intermediate (designated compound 1) is described: β-naphthol and boran trifluoride acetic acid are heated together to obtain the desired naphthodioxaborin.

U.S. Pat. No. 3,896,114 discloses benzo[f]chromones having a formyl, cyano or tetrazole group in the three position, but without substituents on the phenyl ring.

West German Application No. 25 23 194 discloses certain 3-ring chromone derivatives having an acid, ester, amide, cyano or tetrazole substituent on the 3-position, among which there is mentioned trans-3-(8-methoxycarbonyl-4-oxo-4,6,7,8-tetrahydro-cyclopenta[g]-1-benzopyran-3-yl)acrylic acid.

Two-ring chromone structures having various substitutents at the two or three position are also known in the art. For example, U.S. Pat. No. 3,912,760 discloses chromone-3-carboxaldehydes; U.S. Pat. No. 3,849,446 discloses chrmone-3-carboxylic acids; U.S. Pat. No. 3,872,108 discloses chromone-3-acrylic acids; and U.S. Pat. No. 3,862,143 discloses chromone-3-carbonitriles and chromone-3-carboxylic acids.

Based on the previously mentioned work of Reynolds and Van Allan (*J. Het. Chem.* 6:29-35 February, 1969 and 6:375–377 June, 1969), reaction of 2,7-dihydroxynaphthalene with acetic acid and boron trifluoride etherate would be expected to yield a dioxaborin ring on each of the hydroxy groups in the starting material, thus providing a bis(dioxaborin)naphthalene structure (designated Compound 3 in the reaction scheme of the subject invention). However, quite surprisingly, it has now been found that a naphthodioxaborin having an acetoxy substituent is obtained: 3,3-difluoro-1-methyl-naphtho[2,1-d],3,3-dioxaborin-9-ol acetate, designated Compound 2 in the reaction scheme of the subject invention. Compound 2 has been found to be a valuable intermediate for the synthesis of antiallergy agents.

DESCRIPTION OF THE PARTICULAR EMBODIMENTS

This invention relates to compounds of the formula 11:

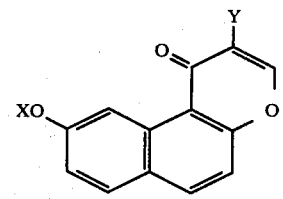

wherein Y is formyl, carboxylic acid, acrylic acid, cyano or tetrazolo; X is hydrogen, lower alkanoyl, or lower alkyl. Also embraced within the scope of this invention are the non-toxic, pharmaceutically acceptable salts of the compounds of the formula 11. A particularly preferred group of compounds are those having the formula 11 wherein Y is carboxylic acid, acrylic acid, cyano, or tetrazolo and X is hydrogen, lower alkanoyl or lower alkyl.

Compounds of the formula 11 are prepared in accordance with the following reaction scheme:

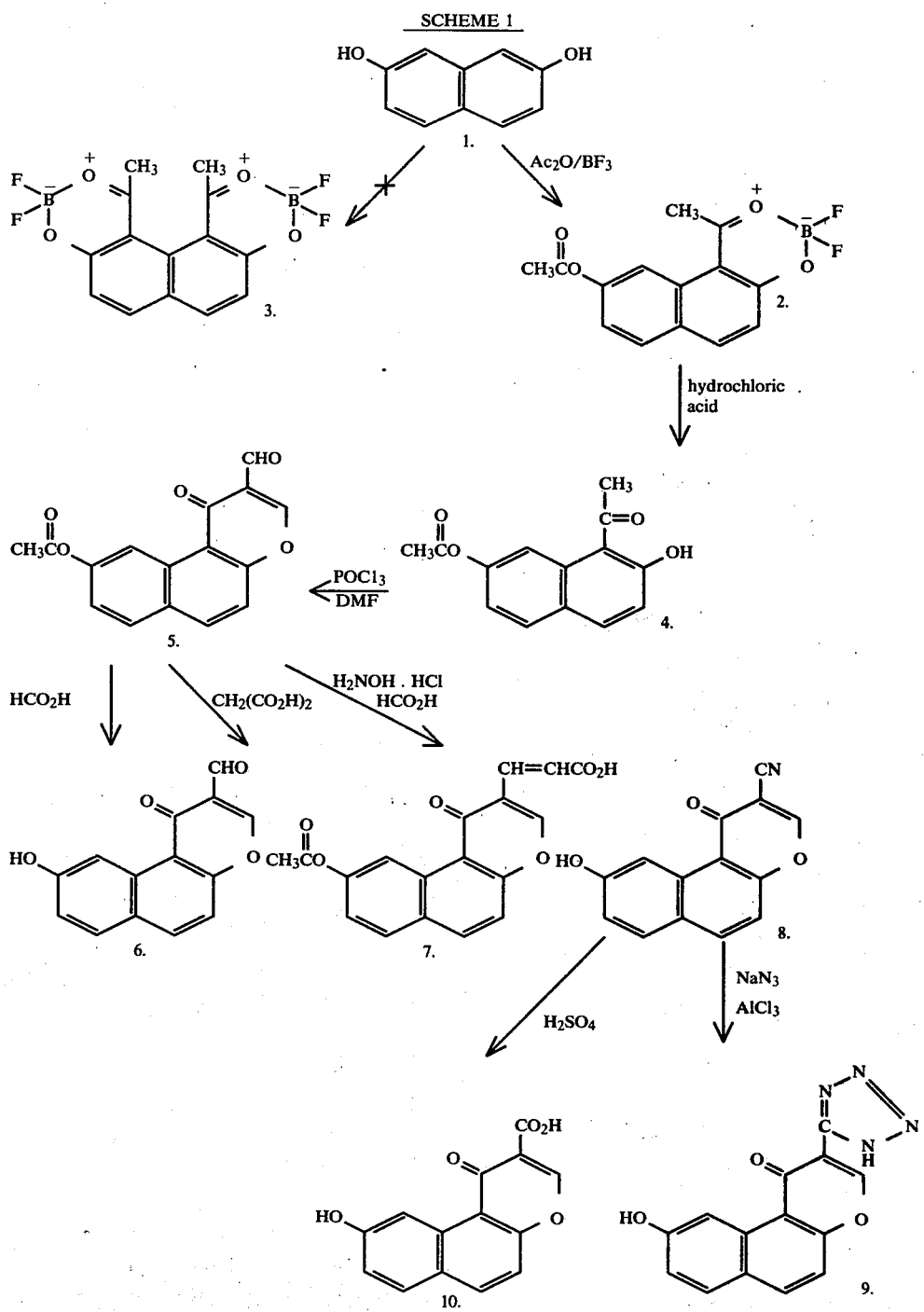

SCHEME 1

Referring to the above reaction scheme, the 2,7-dihydroxynaphthalene starting material 1 is dissolved in a sufficient amount of acetic anhydride to form a solution and boron trifluoride etherate is added thereto. While an excess of acetic anhydride and boron trifluoride etherate may be used in this reaction, the excess has to be removed during purification procedures and is therefore undesirable. Preferably the ratio of compound 1 to acetic anhydride is from about 1 to about 2.5 on a weight/volume basis; and the ratio of compound 1 to boron trifluoride etherate is from about 1 to about 2.5, also on a weight/volume basis. Typically, this reaction mixture is refluxed for at least four hours, preferably for from about four to about ten hours, to form the intermediate 3,3-difluoro-1-methylnaphtho[2,1-d]-1,3,2-dioxiborin-9-ol acetate (Compound 2). One would expect, based on the work of Reynolds and Van Allen (J. Het. Chem. 6:29-35 February, 1969 and 6:375-377 June, 1969) that this reaction would yield the bis adduct compound 3. The production of compound 2 is, therefore, quite surprising.

Compound 2 is treated with an excess of hydrochloric acid, typically by stirring compound 2 in hydrochloric acid at room temperature for at least 18 hours, to obtain 1-acetyl-2,7-naphthalene diol-7-acetate (Compound 4).

Compound 4 is treated with a Vilsmeier reagent prepared from phosphorus oxychloride and dimethylformamide, followed by hydrolysis, to obtain 9-hydroxy-1-oxo-1-H-naphtho[2,1-b]pyran-2-carboxaldehyde acetate (Compound 5).

Compound 5 may be hydrolysed to provide the corresponding 9-hydroxy-1-oxo-1H-naphtho[2,1-b]pyran-2-carboxaldehyde, compound 6. This hydrolysis reaction is conducted by refluxing compound 5 with a lower alkanoic acid such as acetic acid or formic acid or with a dilute mineral acid such as dilute hydrochloric acid or dilute sulfuric acid. Compounds 5 and 6 are intermediates which are used to prepare the remaining compounds of the invention.

Thus, Compound 5 is refluxed with malonic acid in pyridine to obtain [9-(acetyloxy)-1-oxo-1H-naphtho[2,1-b]pyran-2-yl]-2-propenoic acid, compound 7. Additionally, Compound 6 may be refluxed in a similar fashion with malonic acid in pyridine to obtain [9-hydroxy-1-oxo-1H-naphtho[2,1-b]pyran-2-yl]-2-propenoic acid, Compound 7A.

A mixture of compound 5, hydroxylamine hydrochloride and sodium formate is refluxed in formic acid to provide 9-hydroxy-1-oxo-1H-naphtho[2,1-b]pyran-2-carbonitrile, Compound 8.

Aluminum chloride is added to a suspension of Compound 8 and sodium azide in tetrahydrofuran and the reaction is refluxed for from 16 to 30 hours (preferably 24 hours), followed by acidification, typically with hydrochloric acid to obtain 9-hydroxy-2-(1H-tetrazole-5-yl)-1H-naphtho[2,1-b]pyran-1-one, Compound 9. Alternatively refluxing a suspension of Compound 8 in a mineral acid such as hydrochloric acid or sulfuric acid provides 9-hydroxy-1-oxo-1H-naphtho[2,1-b]pyran-2-carboxylic acid, Compound 10.

Compounds 6,7A, 8, 9 and 10 may be alkylated to transform the 9-hydroxy substituent into the corresponding lower alkoxy substituent. Commonly used alkylation procedures such as reaction with diazomethane, dimethylsulfate and potassium carbonate or an alkylhalide and potassium carbonate are suitable for this alkylation reaction. Similarly, Compounds 6, 7A, 8, 9 and 10 may be acylated by refluxing with acetic anhydride or proprionic anhydride to transform the 9-hydroxy group into a lower alkanoyloxy group.

The starting material in the above reaction scheme, 2,7-dihydroxynapthalene is commercially available.

The compounds of this invention having the formula 11 are active in the prevention of allergic conditions (typically, asthmatic reactions) in mammals such as rats, as evidenced by positive results in the passive cutaneous anaphylaxis screen (PCA Test). The PCA screen is a modification of the procedure described by I. Mota, *Life Sciences*, Vol. 4, No. 7: 465–474 (1963) and Z. Ovary and O. Bier, *Proc. Soc. Exptl. Biol. Med.*, 81:584–586 (1952) and provides a measure of the effectiveness of test compounds in inhibiting the release or action of toxic products arising from the combination of reaginic antibodies with specific antigens. These toxic products are causative factors in such disorders as bronchial allergic asthma (extrinsic reagins), exercise asthma, cold asthma, hay fever, perennial allergic rhinitis, food allergies, serum or drug allergies, insect sting allergies, angioneurotic edema, atopic dermatitis, including infantile excema, urticaria, dermographism, dermatoconjunctivitis, acute allergic conjunctivitis, chronic allergic conjunctivitis, and the like.

Inhibition of reaginic antigen/antibody reactions in experimental animals such as rats is regarded as representative of inhibition of human reaginic antigen/antibody reations which occur during allergic episodes.

Thus, the compounds of this invention having the formula 11 are active for the inhibition of reagin-mediated allergic disorders in mammals in need thereof at dose levels of from about 0.5 to about 100 mg/kg of body weight when administered parenterally or by pulmonary administration via the buccal cavity. Thus, for example, 9-hydroxy-2-(1H-tetrazol-5-yl-1H-1H-naphtho[2,1-b]pyran-1-one (the compound of Example 7) shows a 100% inhibition of the allergic response at 0.5 mg/kg when administered intervenously to rats in the passive cutaneous anaphalaxis (PCA) screen. Accordingly, the compounds of this invention having the formula 11 are useful in the treatment of asthma, hay fever and other allergic conditions.

In use, the compounds of the invention having the formula 11 may be combined with parenterally acceptable vehicles, such as gum tragacanth, in saline suspension, to provide dosage forms suitable for parenteral administration.

For pulmonary administration, the compounds of the invention having the formula 11 in dry powder form may be formulated with non-toxic, pharmaceutically acceptable propellants known to the pharmacist's art or they may be dispensed in powder form from a power inhalation device. Compositions in the form of dry powders preferably may include a solid fine powder diluent.

In all of the above formulas, and throughout the specification, the term "lower alkyl" is meant to include lower aliphatic hydrocarbons having 1 to 7 carbon atons (preferably 1 to 4 carbon atoms) in the carbon chain, such as methyl, ethyl, propyl, isopropyl, butyl or isobutyl; the term "halogen" is meant to include bromine, chlorine, iodine and fluorine; and the term "lower alkanoyloxy" is meant to include lower alkanoic acid derivatives having 2 to 3 carbon atoms.

To further illustrate the practice of this invention, the following examples are included.

EXAMPLE 1

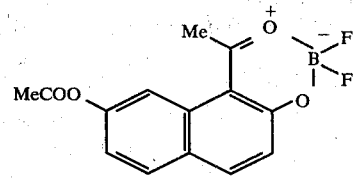

3,3-Difluoro-1-methylnaphtho[2,1-d]-1,3,2-dioxaborin-9-ol acetate

To a solution of 2,7-dihydroxynaphthalene (100 g, 0.625 m) in acetic anhydride (250 ml), boron trifluoride etherate (150 ml) is added dropwise. The reaction is refluxed for 4 hrs. and then cooled. The crystallized product is filtered, washed with ether and sucked dry. Recrystallization from ethyl acetate gives red-brown crystals (118 g, 65%), m.p. 148°–51° C.

Anal. Calcd. for $C_{14}H_{11}BF_2O_4$: C, 57.58; H, 3.80; B, 3.70; F, 13.01. Found: C, 57.58; H, 3.86; B, Qualitatively present; F, 13.03.

NMR (CDCl$_3$) δ 6.98-8.29 (m, 5, ArH), 3.03 (s, 3, CH$_3$), 2.41 (s, 3, OCOCH$_3$).
IR 1773 cm$^{-1}$ (CO).
UV 229 (54,650).

EXAMPLE 2

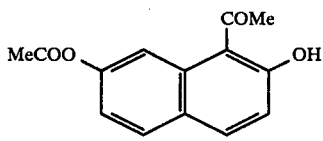

1-Acetyl-2,7-naphthalenediol-7-acetate 3,3-Difluoro-1-methylnaphtho[2,1-d]-1,3,2-dioxaborin-9-ol acetate (50.0 g, 0.171 m) is stirred for 18 hrs. in 2 N hydrochloric acid (300 ml) at room temperature. The product is filtered, washed with portions of water and sucked dry. Recrystallization from isopropyl ether gives orange crystals (37.4 g, 90%), m.p. 74°-77° C.

Anal. Calcd. for C$_{14}$H$_{12}$O$_4$: C, 68.84; H, 4.95. Found: C, 68.61; H, 5.11.

NMR (CDCl$_3$) δ 13.60 (s, 1, OH, exchanges with D$_2$O), 8.1-7.7 and 7.4-7.0 (m, 5, ArH), 2.91 (s, 3, COCH$_3$), 2.42 (s, 3, OCOCH$_3$).
IR 1761 cm$^{-1}$ (CO).
UV 228 (55,200).

EXAMPLE 3

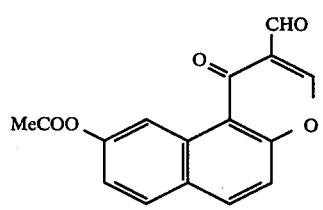

9-Hydroxy-1-oxo-1H-naphtho[2,1-b]pyran-2-carboxaldehyde acetate

A solution of 1-acetyl-2,7-naphthalenediol-7-acetate (50.0 g, 0.204 m) in DMF (300 ml) is cooled to < −20° C. (CO$_2$(s)/acetone). While stirring and maintaining the temperature below −20° C., phosphorous oxychloride (b 154 g, 1.0 m) is added dropwise. The reaction mixture is slowly brought to room temperature and stirred an additional 18 hours. The mixture is poured onto icewater and stirred for 1.5 hrs. The solid product is filtered, washed with water several times, once with acetone and sucked dry. Recrystallization from acetonitrile gives brownish-pink crystals (34.6 g, 60%), m.p. 204°-07° C.

Anal. Calcd. for C$_{16}$H$_{10}$O$_5$: C, 68.08; H, 3.57. Found: C, 68.02; H, 3.73.

NMR (TFA) δ 10.41 (s, 1, CHO), 9.68 (d, 1, C$_5$H), 9.23 (s, 1, C$_2$H), 7.5-8.8 (m, 4, ArH), 2.61 (s, 3, CH$_3$).
IR 1771 cm$^{-1}$ (OCO), 1700 cm$^{-1}$ (CHO), 1650 cm$^{-1}$ (CO).
UV 211 (37,000), 260 (17,500).

EXAMPLE 4

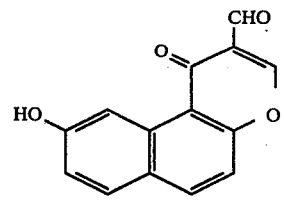

9-Hydroxy-1-oxo-1H-naphtho[2,1-b]pyran-2-carboxaldehyde

Prepared by refluxing 9-hydroxy-1-oxo-1H-naphtho[2,1-b]pyran-2-carboxaldehyde acetate (20.0 g, 0.071 m) in formic acid (250 ml, 88%) for 18 hrs. The product which crystallizes on cooling is filtered, washed with water, with acetone and sucked dry. The crystals are red-brown (16.0 g, 94%), m.p. dec>270° C.

Anal. Calcd. for C$_{14}$H$_8$O$_4$: C, 70.00; H, 3.36. Found: C, 69.77; H, 3.35.

NMR (DMSO) δ 10.48 (v.b.s., 1, OH, exchanges with D$_2$O), 10.30 (s, 1, CHO), 9.30 (m.d., 1, C$_5$H), 8.82 (s, 1, C$_2$H), 8.40-7.15 (m, 4, ArH).
IR 3240 cm$^{-1}$ broad (OH), 1695 cm$^{-1}$ (CO), 1635 cm$^{-1}$ (CO).
UV Qualitative λ$_{max}$ 218; shoulders 276, 344.

EXAMPLE 5

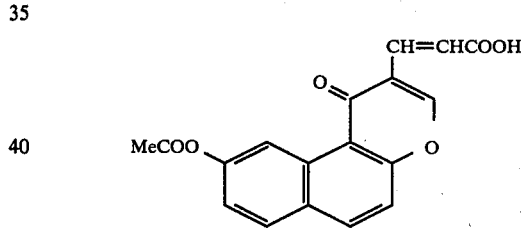

[9-(acetyloxy)-1-oxo-1H-naphtho[2,1-b]pyran-2-yl]-2-propenoic acid

A mixture of 9-hydroxy-1-oxo-1H-naphtho[2,1-b]pyran-2-carboxaldehyde acetate (10.0 g, 0.0354 m) and malonic acid (4.0 g, 0.0354 m) in pyridine (100 ml) is refluxed for 45 minutes. Additional malonic acid (1.0 g, 0.00885 m, 0.25 eq.) is added and the reaction refluxed for 30 minutes. The solvent is removed under reduced pressure to give a sludge from which product crystallizes on the addition of acetone. After filtering the product, recrystallization from DMF gives cocoa crystals (2.75 g, 24%), m.p. dec>290° C.

Anal. Calcd. for C$_{18}$H$_{12}$O$_6$: C, 66.67; H, 3.73. Found: C, 66.50; H, 3.84.

NMR (DMSO) δ 12.7 (v.b.s., 1, OH), 9.65 (m.d., 1, C$_5$H), 8.90 (s, 1, C$_2$H), 6.9-8.6 (m, 6, 4ArH and 2CH), 2.42 (s, 3, CH$_3$).
IR 1747 cm$^{-1}$ (CO), 1670 cm$^{-1}$ (CO), 1656 cm$^{-1}$ (CO).
UV 217 (36,500), 281 (27,700).

EXAMPLE 6

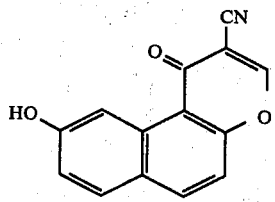

9-Hydroxy-1-oxo-1H-naphtho[2,1-b]pyran-2-carbonitrile

A mixture of 9-hydroxy-1-oxo-1H-naphtho[2,1-b]pyran-2-carboxaldehyde acetate (1 mm), hydroxylamine hydrochloride (1.3 mm) and sodium formate (2 mm) is refluxed for 30 hrs. in formic acid (3 parts). The product crystallize on cooling, is filtered and washed with acetone. The dry crystals are light beige, m.p. 289°-92° C.

Anal. Calcd. for $C_{14}H_7NO_3$: C, 70.89; H, 2.97; N, 5.91. Found: C, 69.87; H, 3.00; N, 6.08.

NMR (DMSO) δ 10.45 (b.s., 1, OH, exchanges with $D_2O$), 9.3 (b.s., 2, ArH), 7.1-8.6 (m, 4, ArH).

IR 3440 cm$^{-1}$ (OH), 2240 cm$^{-1}$ (CN), 1640 cm$^{-1}$ (CO).

UV 216 (43,100); 278 (14,200); 352 (7,000).

EXAMPLE 7

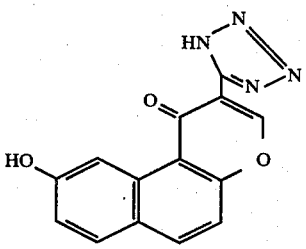

9-Hydroxy-2-(1H-tetrazol-5-yl)-1H-naphtho[2,1-b]pyran-1-one

Aluminum chloride (8.0 g, 0.06 m) is added cautiously to a stirred suspension of 9-hydroxy-2-oxo-1H-naphtho[2,1-b]pyran-2-carbonitrile (8.2 g, 0.0346 m) and sodium azide (8.8 g, 0.135 m) in THF (200 ml). The reaction is refluxed under nitrogen for 24 hrs. After cooling, the reaction is acidified with 5 N HCl. The solids are filtered off and recrystallizes from DMF to give beige crystals (4.6 g, 54.8%), m.p. dec>300° C.

Anal. Calcd. for $C_{14}H_8N_4O_3$: C, 60.00; H, 2.88; N, 19.99. Found: C, 59.09; H, 2.91; N, 19.73.

NMR (DMSO) δ 10.4 (v.b.s., 2, OH and NH, both exchange with $D_2O$), 9.40 (m.d., 1, $C_5H$), 9.28 (s, 1, $C_2H$), 7.1-8.5 (m, 4, ArH).

IR 3360 cm$^{-1}$ (NH)
   3120 cm$^{-1}$ (OH)
   1660 cm$^{-1}$ (CO)
UV 217 (37,500)

EXAMPLE 8

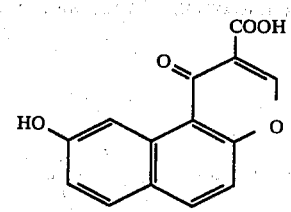

9-Hydroxy-1-oxo-1H-naphtho[2,1-b]pyran-2-carboxylic acid

Prepared by refluxing a suspension of 9-hydroxy-1-oxo-1H-naphtho[2,1-b]pyran-2-carbonitrile (11.8 g, 0.5 m) in 55% sulfuric acid (250 ml) for 30 hrs. After cooling the reaction, the solvent is diluted with cold water, and the product is filtered off and sucked dry. Recrystallization from DMF gives gray-brown crystals (8.2 g, 70%), m.p. 294°-96° C.

Anal. Calcd. for $C_{14}H_8O_5$: C, 65.63; H, 3.15. Found C, 65.42; H, 3.28.

NMR (DMSO) δ 14.46 (b.s., 1, OH, exchanges with $D_2O$), 10.90 (s, 1, OH, exchanges with $D_2O$), 9.16 (s, 1, $C_2H$), 7.4-9.2 (m, 5, ArH).

IR 3230 cm$^{-1}$ (OH) broad, 2700 cm$^{-1}$ (COOH) broad, 1719 cm$^{-1}$ (CO), 1632 cm$^{-1}$ (CO),

UV 227 (41,500), 272 (8,050), 346 (8,400).

We claim:
1. A process for preparing a compound of the formula 9:

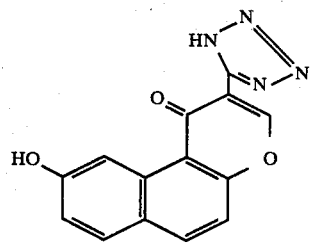

which comprises the steps of:
(A) dissolving a compound of the formula 1:

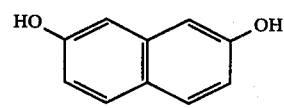

in a sufficient amount of acetic anhydride to form a solution, adding boron trifluoride etherate and refluxing for at least 4 hours to obtain a compound of the formula 2:

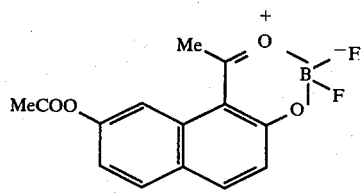

(B) after isolation, reacting compound 2 with hydrochloric acid to obtain a compound of the formula 4:

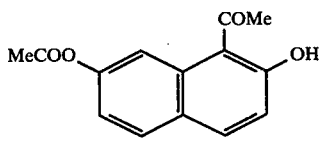

4.

(C) after isolation, treating Compound 4 with a Vilsmeier reagent prepared from phosphorous oxychloride and dimethylformamide, followed by hydrolysis to obtain compound 5:

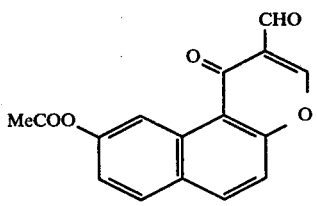

5.

(D) after isolation, refluxing Compound 5 with hydroxylamine hydrochloride and sodium formate in formic acid to obtain Compound 8:

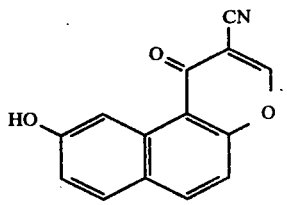

8.

(E) after isolation, adding aluminum chloride to a suspension of Compound 8 and sodium azide in tetrahydrofuran, refluxing for from about 16 to about 30 hours and acidifying to obtain Compound 9.

2. The process according to claim 1 wherein, in step (A), the ratio of Compound 1 to acetic anhydride is from about 1 to about 2.5 on a weight/volume basis; wherein the ratio of Compound 1 to boron trifluoride etherate is from about 1 to about 2.5 on a weight/volume basis; and refluxing is conducted for from about 4 to about 10 hours; and wherein, in Step (B), Compound 2 is reacted with an excess of hydrochloric acid at room temperature with stirring for at least 18 hours.

3. The process according to claim 2 wherein, in an additional step after isolation, Compound 9 is alkylated to transform the 6-hydroxy group into a 6-lower alkoxy group.

4. The process according to claim 2, wherein, in an additional step after isolation, Compound 9 is acylated to transform the 6-hydroxy group into a 6-lower alkanoyloxy group.

* * * * *